United States Patent [19]

Shub et al.

[11] Patent Number: 4,845,031

[45] Date of Patent: Jul. 4, 1989

[54] RECOMBINANT DNA PROCESS FOR PRODUCING USEFUL POLYPEPTIDES

[75] Inventors: David A. Shub, Guilderland; Nancy J. Casna, Croton-on-Hudson, both of N.Y.

[73] Assignee: The Research Foundation of State University of New York, Albany, N.Y.

[21] Appl. No.: 768,975

[22] Filed: Aug. 23, 1985

Related U.S. Application Data

[63] Continuation-in-part of Ser. No. 518,926, Aug. 1, 1983, abandoned.

[51] Int. Cl.$^4$ .................... C12P 21/00; C12N 7/00; C12N 1/20; C12N 15/00
[52] U.S. Cl. .................................. 435/68; 435/235; 435/322; 435/252.3; 435/252.33; 935/31; 935/58; 935/73
[58] Field of Search ...................... 435/5, 68, 6, 172.3, 435/235, 253, 320, 252.3, 252.33; 935/11, 29, 31, 38, 39, 58, 73

[56] References Cited

PUBLICATIONS

Casna, N. et al, *Gene*, vol. 18, pp. 297–307, Sep., 1982.
Shub, D. et al, *American Society for Microbiologists*, Abstract H3, p. 114, Annual Meeting, Mar. 1981.
Simon L. et al, *Proc. Natl. Acad Sci*, vol. 80, pp. 2059–2062, Apr. 1983.
Shub, D. et al, *Gene*, vol. 37, pp. 31–36, Oct. 1985.

*Primary Examiner*—Jayme A. Huleatt
*Attorney, Agent, or Firm*—Roman Saliwanchik; David R. Saliwanchik

[57] ABSTRACT

The subject invention concerns a process for stabilizing foreign proteins within the cell of *E. coli* microbes infected with genetic elements encoding said protein production.

13 Claims, No Drawings

RECOMBINANT DNA PROCESS FOR PRODUCING USEFUL POLYPEPTIDES

This invention was made with Government support under project number PCM82003429 awarded by the National Science Foundation. The Government has certain rights in this invention.

CROSS REFERENCE TO RELATED APPLICATION

This is a continuation-in-part of our copending application Ser. No. 518,926, now abandoned filed on Aug. 1, 1983.

BACKGROUND OF THE INVENTION

The use of *Escherichia coli* bacteria as the host in molecular biology is well known. This microbe apparently was the first prokaryote used for the commercial production of insulin via a cloned gene. *E. coli* as a host for a eukaryotic gene encoding a useful polypeptide or protein is not without defects. One defect which received early extensive notoriety is the production of an endotoxin by *E. coli*. The presence of an endotoxin in a preparation of protein product is not desirable. Thus, extensive work has been done to alleviate this problem. Another defect with use of *E. coli* as a host is that the microbe produces proteases which can destroy susceptible protein product produced by the microbe. This destruction of protein product could lead to the wrong conclusion of low levels of expression of some cloned eukaryotic genes. Generally, the proteases act upon incomplete or abnormal proteins produced by the microbe. However, it is known that *E. coli* proteases also act adversely upon useful foreign proteins, for example, human beta preinterferon and somatostatin.

The publication "Stabilization of proteins by a bacteriophage T4 gene cloned in *Escherichia coli*" by L. D. Simon et al., Proc. Natl. Acad. Sci. USA, Vol 80, pp. 2059-2062, April 1983, discloses the use of a cloned T4 pin gene to stabilize three different kinds of proteins in *E. coli* cells, i.e., (1) incomplete proteins, e.g., puromycyl polypeptides, (2) abnormal but complete proteins, e.g., the λ tsO protein, and (3) labile eukaryotic proteins encoded by genes cloned in *E. coli*, e.g., mature human fibroblast interferon. The process described in this publication involves the use of two apparently hybrid plasmids transformed into the *E. coli* host. One plasmid contains the T4 pin gene whereas the other contains the eukaryotic gene encoding a desired protein product. Though this process allegedly stabilizes the indicated proteins, it is not a desirable commercial process because of the use of two different plasmids in the *E. coli* host. The compatability of such plasmids may not be as stable as desired in the commercial production of useful proteins by recombinant means. Alteration or loss of compatability can wreak havoc on a commercial operation. The process of the subject invention avoids the issue of plasmid incompatability by use of a doubly chimeric plasmid from which a foreign DNA sequence is recombined into a T-even bacteriophage, which is then used to infect the *E. coli* host. The stabilization aspect of the subject invention is not based on the cloning of the T4 pin gene as is the case with the above-disclosed publication process. There are several other publications which concern the field of this invention. Complete citations to these publications are found in the "References" section following the examples.

(1) Revel and Georgopoulous, 1969. Disclosure of phage and bacterial mutants which allow the synthesis of phage DNA with HMC (5-hydroxymethyl cytosine).

(2) Snyder et al., 1976. Same as (1) above except cytosine is used in place of HMC.

(3) Kaplan and Nierlich, 1975. Disclosure that EcoRI functions inefficiently on T4 DNA containing HMC.

(4) Shub and Casna, 1981. Abstract of method for inserting fragments of DNA into bacteriophage T4.

(5) Casna and Shub, 1982. Publication of the cloning procedure disclosed herein. Thus, this publication is hereby incorporated herein by reference thereto.

BRIEF SUMMARY OF THE INVENTION

Disclosed and claimed is a method for stabilizing useful polypeptides, expressed by *E. coli* via a cloned gene, wherein said polypeptides are susceptible to proteases produced within the *E. coli* cell. The polypeptide is expressed by the host using phage regulatory signals. Specifically, as exemplified herein, the subject process comprises:

(1) construction of a chimeric plasmid comprising parts of the rII genes of bacteriophage T4 (DNA fragment) and a portion of the genome of an *E. coli* plasmid, said DNA fragment having sufficient homology to recombine to bacteriophage T4;

(2) in vitro insertion of foreign DNA into the T4 sequence of the chimeric plasmid to give a doubly chimeric plasmid, wherein said DNA fragment from bacteriophage T4 is flanking each end of said foreign DNA;

(3) in vivo recombination between bacteriophage T4 and the doubly chimeric plasmid which transfers the foreign DNA to bacteriophage T4; and, (4) infection of the *E. coli* host with T4 harboring the doubly chimeric plasmid.

The *E. coli* host produces the useful polypeptide, but in the process the host is lysed by bacteriophage T4. The useful polypeptide is then recovered from the medium by standard procedures. Alternatively, if the bacteriophage T4 harbors a mutation resulting in absence or delay of lysis, infected cells containing the useful polypeptide are recovered from the medium, lysed by standard procedures, and the useful polypeptide isolated from the cell lysate. The net effect is that the subject process yields higher levels of foreign polypeptides from the *E. coli* cell.

DETAILED DESCRIPTION OF THE INVENTION

Abbreviations used herein are as follows: bp, base pairs; CAP, catabolite gene activator protein; DTT, dithiothreitol; EtBr, ethidium bromide; glcHMC, glucosyl-5-hydroxymethyl cytosine, HMC, 5-hydroxymethyl cytosine; HMU, 5-hydroxymethyl uracil, kb, kilobase pairs; Xgal, 3-bromo-4-chloro-5-indolyl-β-galactomide; [], indicates plasmid-carrier state.

Publications cited herein appear in the section "References," after the examples.

The construction of the chimeric plasmid comprising bacteriophage T-even DNA and a portion of the genome of an *E. coli* plasmid is exemplified herein by use of T4 DNA and the genome of a modified *E. coli* plasmid. Other bacteriophage T-even DNA can be used so long as the DNA can be stably propagated in *E. coli*, i.e., it is not lethal to *E. coli*. This T-even DNA can be an entire gene or a portion of a gene.

Also, though the examples following disclose the insertion of heterologous DNA into the rIIB gene. of T4, it should be recognized that such DNA can be cloned into the gene or portions of a gene of any T-even bacteriophage. Further, there are a large number of genes in T4 other than the rIIB gene into which the heterologous DNA can be cloned by procedures disclosed herein or others well known in the art, as long as the function of such other T4 genes is not required for propagation of the bacteriophage.

The subject process is exemplified by use of bacteriophage T4 as the cloning vehicle. It should be understood that other T-even bacteriophages, laboratory or naturally-occurring related strains, can be used to infect the *E. coli* host, so long as they are biologically equivalent to T4, i.e., can serve as a DNA-cloning vehicle in substantially the same manner as disclosed herein for T4.

Any *E. coli* can be used as the host microbe so long as it is sensitive to infection by T-even bacteriophage. Disclosed herein is the use of an amber suppressor mutant *E. coli* because an amber mutant phage was used. This procedure, which is well known in the art, was used solely to enhance sensitivity of the selection process. See Singer et al. (Singer, B. S., Gold, L., Shinedling, S. T., Colkitt, M., Hunter, L. R., Pribnow, D. and Nelson, M. A. [1981]J. Mol. Biol. 149:405-432) which discloses essentially the same procedure to obtain deletion mutants in the rII genes. It should be understood that it is not essential to use an amber suppressor mutant *E. coli* host to practice the subject invention, because the high frequency of transfer of the insert from plasmid to phage allows isolation of chimeric T4 using well-known methods of plaque hybridization, or by detecting the protein product of the insert DNA by enzymatic or immunochemical assay.

Suitable *E. coli* hosts which can be used in the subject invention are numerous and available to the public from established repositories, for example, the American Type Culture Collection (ATCC) in Rockville, MD. Further, the Yale University *E. coli* Genetic Stock Center (ECGSC) makes subcultures available to the public upon request.

Specific *E. coli* hosts disclosed herein are available to the public from the following repositories:
*E. coli* 3000X111--ECGSC 5263
*E. coli* C600--ATCC 23724
*E. coli* 1078--NRRL B-15476. (This NRRL deposit is referred to infra.)

It should also be recognized that though *E. coli* is the preferred host, other Gram negative bacteria, for example, species of Shigella, can be employed as the host so long as they are sensitive to infection by T-even bacteriophage. Such Shigella bacteria also are available to the public from repositories, for example, ATCC. The use of other Gram negative bacterial hosts would follow the same procedures as disclosed herein for *E. coli* with obvious adjustments to culturing and containment for different bacteria. These culturing and containment requirements are well known to a person skilled in the art.

MATERIALS AND METHODS (a) *E. coli* strains, phage strains and plasmids

*E. coli* 1078 (C600 r⁻m⁺ supE44 thr⁻ leu⁻ thi⁻) was used as a recipient for transformation and propagation of plasmid DNA. HR141A (U95 rgl⁻) was used to prepare HMC DNA (Revel and Georgopoulos, 1969). For plating phage: CR63 (suI$^+_{am}$); CR63 (λ) (suI$_{am}^+$); BB(su⁰; permissive for rescue of gene $30_{am}^-$ by mutations in rII), were used. T4 strain C104B (gene $30_{am}^-$)p used for gene 30 rescue experiments.

Plasmid pOP203-1 is a pMB9 derivative that contains a 203-bp HaeIII fragment (containing the UV5 promoter mutation) of the lactose region of *E. coli*, inserted at the EcoRI site (Backman et al., 1976). Plasmid pBR322 (H23r⁺) contains an 873-bp fragment of the intercistronic region of the rII genes of T4, inserted at the HindIII site of pBR322 (Pribnow et al., 1981).

(b) Enzymes and other reagents

Restriction endonucleases EcoRI, AluI, BglII, HhaI, BamHI (New England Biolabs), HinfI (Bethesda Research labs), and HindII and TaqI (Boehringer Mannheim) were used according to the specifications supplied by the vendor, except that TaqI was used at 4 units per microgram of T4 DNA for 3 hours in order to achieve complete reactions. EcoRI* reactions were carried out at a final concentration of 25 mM Tris.HCl, pH 8.5; 2 mM MgCl$_2$ (Polisky et al., 1975), S$_I$ nuclease (Boehringer Mannheim) reactions were performed with 8 μg of EcoRI-cut pOP203-1 DNA and 80 units of enzyme, in 0.2 ml of 0.2 mM ZnSO$_{40}$, 50 mM sodium acetate pH 4.5, 100 mM NaCl for 30 min at 37° C. T4 DNA ligase (BRL) was reacted at a final concentration of 50 mM Tris.HCl pH 7.5, 100 mM MgCl$_2$, 20 mM DTT, 1 mM ATP overnight at 4° C with 1 unit/μg of DNA. Xgal was dissolved in dimethylformamide to 2% and 50 μl was used per agar plate. Klenow fragment of DNA polymerase I (Boehringer Mannheim) was used at 1 unit/μg DNA, to fill in staggered ends at a final concentration of 6.6 mM Tris.HCL pH 7.5, 6.6 mM NaCl, 6.6 mM MgCl$_2$, 6.6 mM DTT and 0.1 mM of each dNTP.

(c) Gel electrophoresis

Analytical agarose gels (1%) were run at a constant voltage of 150 V for an average of 16 h in buffer of final concentration 40 mM Tris.HCl pH 7.9, 20 mM sodium acetate, 1 mM EDTA. The gels were stained with 1 μg/ml EtBr for 15 min and photographed by transillumination with longwave UV light.

(d) Preparation of DNA and transformation

HMC T4 DNA was prepared by diluting the progeny of an infection of *E. coli* HR141A, concentrated and purified by a CsCl step gradient, to an A$_{260}$ of 20. The phage were then extracted twice with an equal volume of phenol saturated with 0.1 M Tris.HCl pH 7.9 and the aqueous phase was dialyzed at 4° C. overnight into 10 mM Tris.HCl pH 7.9, 0.1 M NaCl, 0.1 mM EDTA.

Plasmid and M13 RF DNAs were prepared by the Triton-X cleared lysate procedure of Katz et al. (1973) and banded on a CsCl-EtBr buoyant density gradient. Small preps were prepared in the same way, omitting the CsCl gradient and replacing it with a 30 min incubation at 37° C. in 100 μg/ml proteinase K, followed by two extractions with an equal volume of phenol, and ethanol precipitation. Transformation was carried out as described by Cohen et al. (1972).

As disclosed above, the subject process is useful to stabilize foreign proteins in the *E. coli* cell. Proteins which are susceptible to the proteases within the *E. coli* cell are numerous and well known. Examples are somatostatin and human beta preinterferon. Other genes encoding sequences for the production of useful foreign proteins can be inserted into T4 by use of the techniques disclosed herein with suitable obvious adjustments which are well within the skill of those in the art. As is evident, such an inserted gene would contain the essential control signals (promoter and ribosome initiation site) which are actively recognized in a T4 infected cell, i.e., signals derived from T4 itself. Where it is desired to transfer large DNA inserts into T4, appropriate deletion mutants of T4 will be used. Such deletion mutants of T4 are well known and readily available to persons skilled in the art. Thus upon the obtention of suitable T4 strains with compensatory deletions to accommodate various sizes of DNA gene inserts, a person skilled in the art, with the subject disclosure, is enabled to clone various genes encoding useful foreign proteins into T-even bacteriophage. The final result is the expression of the useful foreign protein without degradation by the host *E. coli* cell. The subject process is also useful in the screening of DNA banks by well-known procedures and antigenic methods. The stabilization of the produced proteins enhances the efficiency of such methods since lower levels of protein can be detected.

The following cultures have been deposited in the permanent collection of the Northern Regional Research Center (NRRL), U.S. Department of Agriculture, Peoria, Ill., USA.

*E. coli* RR1 [pBR322(H23r+)]
   NRRL B-15475
   Deposited on July 7, 1983
E coli 1078 (pNC7)
   NRRL B-15477
   Deposited on July 7, 1983
E coli 1078 (pNC7lac2)
   NRRL B-15478
   Deposited on July 7, 1983
E. coli 1078
   NRRL B-15476
   Deposited on July 7, 1983

Plasmid pBR322 is a well-known and available plasmid. It is maintained in the *E. coli* host ATCC 37017. Purified pBR322 DNA, pNC7 DNA and pNC7lac2 DNA can be obtained from their *E. coli* hosts by well-known procedures, e.g., using the cleared lysateisopycnic density gradient procedures.

The above culture deposits are available to the public upon the grant of a patent which discloses the assigned accession numbers in conjunction with the invention described herein. It should be understood that the availability of these deposits does not constitute a license to practice the subject invention in derogation of patent rights granted for the subject invention by governmental action.

Following are examples which illustrate procedures, including the best mode, for practicing the invention, and products produced thereby. These examples should not be construed as limiting. All percentages are by weight and solvent mixture proportions are by volume unless otherwise noted.

EXAMPLE 1

Construction and characterization of plasmid pNC7 pBR322(H23r+) contains an 873-bp HindIII fragment of the rII genes of T4 (HH870) inserted into the single HindIII site of pBR322. This fragment spans the carboxy terminal coding region of rIIA, the 11-bp intercistronic region and the amino terminal coding region of the rIIB gene. The sequences of pBR322 (Sutcliffe, 1978) and HH870 (Pribnow et al., 1981) are known, enabling restriction enzyme sites and sizes of fragments to be predicted for the chimeric plasmid. The orientation of HH870 within pBR322 was easily determined by a double digestion with the restriction endonucleases EcoRI and HincII. The smallest HincII fragment of H23r+ was found to harbor the EcoRI site, revealing the orientation to be counterclockwise from rIIA to B in the plasmid. A convenient site for insertion of DNA fragments to be cloned into T4, within HH870, is a HincII site located 110-bp into the rIIB gene, the only HincII site in HH870. There are two additional HincII sites in pBR322, one in the ampicillin-resistance gene (at position 3907) and another at position 652. To facilitate insertion of fragments of interest into the HincII site located within HH870, the site located at position 652, which is also recognized by SalI, was eliminated. After cleaving with SalI, 5' single-strand extensions were filled in with the four deoxynucleotide triphosphates and Klenow fragment of DNA polymerase I, and the resulting ends were ligated back together. During this procedure plasmids were isolated that contained deletions of various sizes. One of these, pNC7, was chosen to be used for the remainder of the experiments.

The plasmid pNC7 is about 3.67 kb in length and confers resistance to ampicillin. Extensive restriction analyses were performed on pNC7, pBR322 and the parental plasmid H23r+ to estimate the size and endpoints of the pNC7 deletion. As expected, the SalI site at position 650 of pBR322 and the HincII site at position 652, were lost. In the counterclockwise direction, all restriction sites remained intact, including the HinfI site at position 631 of pBR322. In the clockwise direction, the HhaI site at position 2180 was clearly lost, while the site at 2210 was still intact. Thus the clockwise endpoint of the deletion is at position 2194±13 bp. Size analysis of the new AluI and HinfI restriction fragments generated by the deletion, is consistent with a deletion of about 1546 bp. This suggests that the deletion extends in a single clockwise direction from the SalI site to approximately position 2196 of pBR322.

EXAMPLE 2

Insertion of the lac fragment into plasmid pNC7

A fragment of the control region of the lactose operon of *E. coli* was chosen as the DNA to be cloned, due to its known nucleotide sequence (Maizels, 1973; Dickson et al., 1975; Farabaugh, 1978), ease of availability, and the advantages it offers for selection. A 203-bp fragment that begins 17 codons from the end of the lacI gene and extends through the operator/promoter region to the 8th codon of the lacZ gene, was removed from the plasmid pOP203-1 by EcoRI digestion. This mixture of fragments was then treated with S1 nuclease to remove the 4-bp 5' single-strand extensions, phenol extracted and blunt-end ligated to pNC7 plasmid, which had been partially cleaved with HincII to yield mostly linear molecules. The ligated mixture was then used to transform *E. coli* 1078 and the transformants were selected on plates containing ampicillin, thereby selecting against plasmids containing fragments inserted into the remaining HincII site in the pBR322 DNA. Xgal was also included in the plates to allow easy identification of colonies that contained plasmids harboring the lac control fragment. Because this plasmid is present in high copy number, the presence of the lac operator on the plasmid is sufficient to titrate all the lac repressor from the chromosomal operator. The result i constitutive production of β-galactoside, which cleaves the chromogenic substrate, generating bright blue colonies on the plate.

Promising candidates were chosen from the ampicillin-Xgal plates and plasmid DNA was isolated in sufficient quantities to do several restriction enzyme reactions. The plasmid pNC7lac2 was determined to be approximately 200 bp larger than pNC7 by restriction analysis with EcoRI, HindIII and BglI. Digestion with AluI was consistent with this insertion being the lac fragment, as the internal lac AluI fragments were present, and the pNC7 fragments with the adjoining lac ends were the appropriate sizes. HinfI, which cleaves near both ends of the lac DNA, also generated a fragment of the expected size. A HhaI restriction site asymmetrically located within the 203-bp lac fragment allowed determination of the orientation of the lac fragment within the rII region of the plasmid. It was found to be oriented such that the operator/ promoter region would drive transcription toward the rIIB gene, or in a counterclockwise direction from lacI to lacZ in the plasmid

EXAMPLE 3

Transfer of the lac fragment into T4

Mattson et al. (1977) reported that recombination can occur in vivo between E. coli plasmids containing T4 sequences and the T4 genome. Recombination across the rII sequences of pNC7lac2 allows transfer of the lac sequences from the plasmid into the phage genome. The lac fragment contains translational termination codons in all reading frames (Dickson et al., 1975; Farabaugh, 1978). Since the HincII restriction site is within the coding region of the rIIB gene, lac insertion would cause the recombinant phage to be rIIB−. It has previously been shown (Berger and Kozinski, 1969; Ebisuzaki and Campbell, 1969; Karam, 1969) that mutations in gene 30 (DNA ligase) of T4, normally a lethal phenotype, can be suppressed on certain strains of E. coli by a compensatory mutation in rII. Although the mechanism remains undefined, this offers an easy means of selecting T4 phage that have acquired the lac insertion. The transfer and selection was accomplished in one step by infecting an amber suppressor E. coli strain containing the plasmid (l078pNC7lac2]) with Cl04B, a T4 strain that is rII+30$_{am}$−. Progeny of the infection were selected on E. coli strain BB, which does not suppress amber mutations, but does allow suppression of gene 30 mutations by mutations in rII (Karam and Barker, 1971). Frequencies of rescue of the gene 30 mutation (the fraction of total phage after the infection that could grow on the non-amber suppressing strain) were in the range of $1 \times 10^{-2}$ to $4 \times 10^{-3}$ (Table I), which was a 10− to 18-fold increase over the frequency for the progeny produced during an infection of a strain bearing the plasmid-containing wild-type rII DNA.

TABLE I

Efficiency of plating of C104B on plasmid-containing E. coli strains
E. coli 1078 carrying the plasmid indicated was infected with C104B at a multiplicity of 1.0. After 5 min the culture was diluted in H broth (Steinberg and Edgar, 1962) and incubated at 30° C. The culture was lysed after 2 h and progeny of the infection plated. The efficiency of plating is the fraction of total progeny (plaques on E. coli B$_{40}$suI+) that could plate on the non-amber suppressing strain E. coli BB.

| Experiment | Efficiency of plating | |
|---|---|---|
| | pNC7($\times 10^{-4}$) | pNC7lac2 |
| 1 | 2.4 | $3.5 \times 10^{-3}$ |
| 2 | 4.9 | $9.0 \times 10^{-3}$ |
| 3 | 7.0 | $1.1 \times 10^{-2}$ |
| 4 | 4.0 | $4.0 \times 10^{-3}$ |

Phage containing the lac insert were quite stable. During the preparation of a phage stock from a single isolated plaque, revertants, identified by the ability to grow on CR63 (λ), occurred at a frequency of about $1 \times 10^{-9}$. Analysis of the proteins produced by four of these revertants, by gel electrophoresis, showed rIIB proteins of molecular weight indistinguishable from wild type. Therefore, revertants arise by an almost exact, in-frame deletion of the lac insert.

EXAMPLE 4

The lac fragment is part of the T4 genome

Evidence that the mutation mapping at the rIIB HincII site is, in fact, due to insertion of the 203-bp lac DNA was provided by restriction analysis. T4 DNA in its native form is completely substituted with glcHMC. HMC DNA can be obtained by infecting an E. coli strain that lacks UDP-glucose pyrophosphorylase and the host nuclease which degrades HMC DNA (Revel and Georgopoulos, 1969). Unmodified cytosine-containing T4 DNA can also be obtained, but this requires mutations in additional phage genes (Snyder et al., 1976). Two restriction endonucleases have recently been found to function on native T4 DNA: EcoRV and TaqI. Two additional enzymes can function on HMC T4 DNA: EcoRI (Kaplan and Nierlich, 1975) and XbaI. To obtain complete digestion of HMC T4 DNA with EcoRI requires large amounts of enzyme and long digestion times. Work on bacteriophage SP0l DNA, which also contains a modified base (thymine is completely replaced by HMU), indicated that the same digestion pattern generated under EcoRI conditions, can be generated under EcoRI* conditions in a shorter length of time with much less enzyme (Cregg and Stewart, 1978). Digestion of HMC T4 DNA under EcoRI* conditions showed this same increase in reaction rate without loss of specificity.

HMC T4 DNA was prepared from wild type and lac insert phage. Digestion of these DNAs under EcoRI* conditions reveals a shift in the position of a band at about 5.4 kb in wild-type DNA, to 5.6 kb in the lac-containing DNA. It was fortuitous that the EcoRI* bands containing the rII genes migrate to a position that is relatively free from other bands that might mask the change in M$_r$-value. Previously the best estimate for the size of the EcoRI fragment containing the rII genes was about 4.4 kb (Selzer et al., 1978), which was determined from the size of an EcoRI fragment of cytosine-containing T4 DNA. To obtain unmodified DNA a deletion was introduced in the region adjacent to the rII genes;

therefore, the size of the wild-type fragment was based upon the estimated size of the deletion used.

HMC DNA from wild-type and lac insertion phage was also digested with restriction endonuclease TaqI. Again a shift in the size of a band is apparent in the lac-containing DNA. Material from the wild-type digest, migrating as part of a band at 1520 bp, migrates as part of a band at 1730 bp in the digest from T4 rIIBlac2. These sizes are expected to be slight overestimates, since the $M_r$ standards from which they were computed contained cytosine rather than HMC. The sizes are consistent with those expected. The lac203 DNA was inserted into the unique HincII cleavage site (between bp 543 and 544) of HH870. The latter has only one TaqI recognition sequence, about 20 bp from the right end (Pribnow et al., 1981). The HindIII fragment immediately to the left of HH870 has about 400 bp (Selzer et al., 1978) and is not cut by TaqI. Thus, the TaqI fragment expected to be altered by insertion should contain at least 1200 bp. Since the lac DNA used has no cleavage site for TaqI (Maizels, 1973; Dickson et al., 1975; Farabaugh, 1978), we would expect the insertion to result in an increase of 203 bp. To prove that these two bands do indeed contain the rII and lac DNA, separate Southern (1975) hybridizations were done to duplicate lanes of this gel with the plasmid pNC7 as a probe for the rII DNA and M13mp2 RF as a probe for the presence of the lac fragment. An autoradiogram of the hybridization with the pNC7 probe shows that these two bands are the only ones containing DNA complementary to HH870. An autoradiogram of the hybridization to the same gel with M13mp2 RF as a probe shows that the lac fragment is indeed physically inserted into the rII genes

EXAMPLE 5

Expression of large DNA inserted into phage containing compensatory deletions pNC83 is a plasmid which was derived from pNC7, with the following alterations: The PstI and HincII restriction sites in the gene for ampicillin resistance are absent (Vieira and Messing, 1982), and the unique restriction sites for enzymes BamHI and EcoRI were eliminated in consecutive steps by cutting with BamHI, filling in with Klenow fragment of DNA polymerase I, ligating with T4 ligase, transforming competent E. coli 1078 to ampicillin resistance, and repeating the entire process starting with EcoRI. This results in a unique HincII restriction site in pNC83, in the rIIB sequence cloned into the plasmid. pMC1871 is a derivative of pBR322, where the coding sequence of an enzymatically active β-galactosidase gene has been cloned into its PstI site, flanked by "polylinker" sequences containing recognition sites for a number of restriction endonucleases (Shapira et al., 1983). pMC1871 was cut with SalI (which cuts after the end of the β-galactosidase gene), filled in with Klenow fragment of DNA polymerase I, and then cut with SmaI (which cuts between codons, near the beginning of the β-galactosidase gene). pNC83 was cut with HincII, which cuts between codons in the rIIB portion of the sequence. The DNAs were mixed, ligated with T4 DNA ligase, and used to transform E. coli 3000XIII (which contains a deletion of the lac region) to ampicillin resistance on plates containing ampicillin and Xgal (an indicator substrate which turns blue when cleaved by β-galactosidase). A blue colony was picked, and the plasmid it contained was called pSSZ1. pSSZ1 contains the sequence of a gene encoding an enzymatically active β-galactosidase, fused (in the correct reading frame) to the translation initiation sequence and first 37 codons of the rIIB gene. This gene fusion was transferred into a T4 phage containing a compensatory deletion, saΔ9, which is lacking the DNA between the D1 and ac genes (Depew et al., 1975). Progeny of an infection of E. coli 3000XIII (pSSZ1) by saΔ9 phage were plated on a lawn of E. coli 3000XIII containing Xgal. Between 1% and 0.1% of the plaques were bright blue. Phage prepared from one of these plaques (saΔ9, rIIB(SSZ1)) were mixed with an equal number of saΔ9 phage and plated on E. coli 3000XIII, with Xgal. As expected, about half the plaques were blue. The plate was subjected to the plaque hybridization procedure of Benton and Davis (1977), with radioactive probe prepared from nick-translated pMC1871. There was 100% coincidence between the blue plaques and those that hybridized to the probe. Thus, a foreign DNA sequence inserted into T4 can be detected by plaque hybridization, long sequences can be inserted into phage having a compensatory deletion, and a useful polypeptide encoded in the foreign DNA can be expressed in E. coli cells. These E. coli can be Su+ or Su−, dependent on the presence of nonsense mutations in the T4 phage (see Example 3, above). Su+ cells contain a suppressor mutation, whereas Su- cells are wild type, i.e., they do not contain a suppressor mutation In addition to saΔ9, the T4 phage eG506,S (Black, 1974) and del(39-56)-12 (Homyk and Weil, 1974) have been used as compensatory deletions. These three phage, which have deletions of several kb in different regions of the T4 genome, are all able to act as recipient for the β-galactosidase gene, and to express it as an active enzyme. The frequency of incorporation of the gene was highest for saΔ9.

REFERENCES

Backman, K., Ptashne, M. and Gilbert, W.: Construction of plasmids carrying the cI gene of bacteriophage λ. Proc. Natl. Acad. Sci. USA 73 (1976) 487-560.

Barnett, L., Brenner, S., Crick, F. H. C., Shulman, R. G. and Watts-Tobin, R. J.: Phase shift and other mutants in the first part of the rIIB cistron of bacteriophage T4. Phil. Trans. Royal Soc. London, Series B 252 (1967) 487-560

Benton, W. D. and Davis, R. W. : Screening λgt recombinant clones by hybridization to single plaques in situ. Science 196 (1977) 180-182.

Benzer, S.: On the topography of the genetic fine structure. Proc. Natl. Acad. Sci. USA 45 (1959) 1607-1620.

Benzer, S. and Champe, S. P.: A change from nonsense to sense in the genetic code. Proc. Natl. Acad. Sci. USA 48 (1962) 1114-1121.

Berger, H. and Kozinski, A. W.: Suppression of T4D ligase mutations by rIIA and rIIB mutations. Proc. Natl. Acad. Sci. USA 64 (1969) 897-904.

Black, L. W.: Bacteriophage T4 internal protein mutants: isolation and properties. Virology 60 (1974) 166-179.

Casna, N. J. and Shub, D. A.: Bacteriophage T4 as a generalized DNA-cloning vehicle. Gene 18 (1982) 297-307.

Cohen, S. N., Chang, A. C. Y. and Hsu, L.: Nonchromosomal antibiotic resistance in bacteria: genetic transformation of Escherichia coli by R-factor DNA. Proc. Natl. Acad. Sci. USA 69 (1972) 2110-2114.

Cregg, J. M. and Stewart, C. R.: EcoRI cleavage of DNA from *Bacillus subtilis* phage SP01. Virology 85 (1978) 601–605.

Depew, R. E., Snopek, T. J. and Cozzarelli, N.: Characteriaztion of a new class of deletions of the D region of the bacteriophage T4 genome. Virology 64 (1975) 144–152.

Dickson, R. C., Abelson, J., Barnes, W. M. and Reznikoff, W. S.: Genetic regulation: the lac control region. Science 187 (1975) 27–35.

Ebisuzaki, K. and Campbell, L.: On the role of ligase in genetic recombination in bacteriophage T4. Virology 38 (1969) 701–703.

Farabaugh, P. J.: Sequence of the lacI gene. Nature 274 (1978) 765–769.

Homyk, T. Jr. and Weil, J.: Deletion analysis of two nonessential regions of the T4 genome. Virology 61 (1974) 505–523.

Kaplan, D. A. and Nierlich, D. P.: Cleavage of nonglucosylated bacteriophage T4 deoxyribonucleic acid by restriction endonuclease EcoRI. J. Biol. Chem. 250 (1975) 2395–2397.

Karam, J. D.: DNA replication by phage T4rII mutants without polynucleotide ligase (gene 30). Biochem. Biophys. Res. Commun. 37 (1969) 416–422.

Karam, J. D. and Barker, B.: Properties of bacteriophage T4 mutants defective in gene 30 (deoxyribonucleic acid ligase) and the rII gene. J. Virol. ? 7 (1971) 260–266.

Katz, L., Kingsbury, D.T. and Helinski, D. R.: Stimulation by cyclic adenosine monophosphate of plasmid deoxyribonucleic acid replication and catabolite repression of the plasmid deoxyribonucleic acidprotein complex. J. acteriol. 114 (1973) 577–591.

-Maizels, N. M.: The nucleotide sequence of the lactose messenger ribonucleic acid transcribed from the UV5 promoter mutant of *Escherichia coli*. Proc. Natl. Acad. Sci. USA 70 (1973) 3585–3589.

Mattson, T., Van Houwe, G., Bole, A., Selzer, G. and Epstein, R.: Genetic identification of cloned fragments of bacteriophage T4 DNA and complementation by some clones containing early T4 genes. Mol. Gen. Genet. 154 (1977) 319–326.

Polisky, B., Green, P., Garfin, D. E., McCarthy, B. J., Goodman, H. M. and Boyer, H. W.: Specificity of substrate recognition by the EcoRI restriction endonuclease. Proc. Natl. Acad. Sci. USA 72 (1975) 3310–3314.

Pribnow, D., Sigurdson, D. C., Gold, L" Singer, B. S., Napoli, C., Brosius, J., Dull, T. J. and Noller, H. F.: rII cistrons of bacteriophage T4. DNA sequence around the intercistronic divide and positions of genetic landmarks. J. Mol. Biol. 148 (1981) 337–376.

Revel, H. and Georgopoulos, C. P.: Restriction of nonglucosylated T-even bacteriophages by prophage P1. Virology 39 (1969) 1–17.

Selzer, G., Bolle, A., Krisch, H. and Epstein, R.: Construction and properties of recombinant plasmids containing the rII genes of bacteriophage T4. Molec. Gen. Genet. 159 (1978) 301–309.

Shapira, S. K., Chou, J., Richaud, F. U. and Casadaban, M. J.: New versatile vectors for expression of hybrid proteins coded by a cloned gene fused to lacZ gene sequences encoding an enzymatically active carboxyterminal portion of β-galactosidase. Gene 25 (1983) 71–82.

Shub, D. A. and Casna, N. J.: Bacteriophage T4 as a generalized DNA cloning vector. Amer. Soc. Microbiol. Abstracts of the Annual Meeting (1981) H3, 114.

Simon, L. D., et al. Stabilization of proteins by a bacteriophage T4 gene cloned in *Escherichia coli*. Proc. Natl. Acad. Sci. USA 80 (1983) 2059–2062.

Snyder, L., Gold, L. and Kutter, E.: A gene of bacteriophage T4 whose product prevents true late transcription on cytosine-containing T4 DNA. Proc. Natl. Acad. Sci. USA 73 (1976) 3098–3102.

Southern, E. M.: Detection of specific sequences among DNA fragments separated by gel electrophoresis. J. Mol. Biol. 98 (1975) 503–517.

Steinberg, C. M. and Edgar, R. S.: A critical test of a current theory of genetic recombination in bacteriophage. Genetics 47 (1962) 187–208.

Sutcliffe, G.: pBR322 restriction map derived from the DNA sequence: accurate DNA size markers up to 4361 nucleotide pairs long. Nucl. Acids Res. 5 (1978) 2721–2728.

Vieira, J. and Messing, J.: The pUC plasmids, an M13mp7-derived system for insertion mutagenesis and sequencing with synthetic universal primers. Gene 19 (1982) 259–268.

We claim:

1. We process for producing polypeptides expressed by *E. coli* wherein said polypeptides are susceptible to proteases produced within said *E. coli* which comprises:
   (a) constructing a chimeric plasmid by combining an E- coli plasmid with a DNA fragment from a T-even bacteriophage, said fragment having sufficient homology to recombine into a T-even gene;
   (b) creating a doubly chimeric plasmid by in vitro insertion of foreign DNA encoding a useful polypeptide into said chimeric plasmid so that said DNA fragment from a T-even bacteriophage is flanking each end of said foreign DNA encoding a useful polypeptide;
   (c) introducing said doubly chimeric plasmid and a T-even bacteriophage into a first *E. coli* such that said foreign DNA encoding a useful polypeptide is transferred to the T-even phage as a result of *in vivo* recombination;
   (d) infecting a second *E. coli* with said T-even phage comprising said foreign DNA ending a useful polypeptide;
   (e) producing said useful polypeptide by culturing said second *E. coli*;
   (f) lysing said second *E. coli*; and
   (g) recovering said useful polypeptide.

2. A process, according to claim 1, step (a), wherein said DNA fragment from a T-even bacteriophage is stably propagated in an *E. coli*.

3. A process, according to claim 2, wherein said DNA is an entire gene or genes, or a portion of a gene.

4. A process, according to claim 3, wherein said genes are the rIIA or rIIB genes of bacteriophage T4.

5. A process, according to claim 1, wherein said T-even bacteriophage is bacteriophage T4.

6. A process, according to claim 1, wherein said *E. coli* plasmid is pBR322(H23r+).

7. A process, according to claim 1, wherein said foreign DNA insert is a eukaryotic gene encoding a useful polypeptide.

8. A process, according to claim 1, wherein said *E. coli* is *E. coli* 1078 or *E. coli* C600.

9. Plasmid pNC7 which (1) contains a portion of the genome of plasmid pBR322(H23r+) including an 873-bp HindIII fragment of the rII genes of bacteriophage T4 (HH870) inserted into the single HindIII site of pBR322, (2) is about 3.67 kb in length, and (3) confers resistance to ampicillin.

10. Plasmid pNC7lac2 which (1) contains a portion of the genome of plasmid pBR322(H23r+) including an 873-bp HindIII fragment of the rII genes of bacteriophage T4 (HH870) inserted into the single HindIII site of pBR322, (2) confers resistance to ampicillin, and (3) makes host cells carrying a functional β-galactosidase gene, a constitutive producer of β-galactoside.

11. A process for producing polypeptides expressed by a Gram negative bacterium wherein said polypeptides are susceptible to proteases produced within said Gram negative bacterium which comprises:
   (a) constructing a chimeric plasmid by combining a Gram negative bacterium plasmid with a DNA fragment from a T-even bacteriophage, said fragment having sufficient homology to recombine into a T-even gene;
   (b) creating a doubly chimeric plasmid by in vitro insertion of foreign DNA encoding a useful polypeptide into said chimeric plasmid so that said DNA fragment from a T-even bacteriophage is flanking each end of said foreign DNA encoding a useful polypeptide;
   (c) introducing said doubly chimeric plasmid and a T-even bacteriophage into a first gram negative bacterium, such that said foreign DNA encoding a useful polypeptide is transferred to the T-even phage as a result of *in vivo* recombination;
   (d) infecting a second Gram negative bacterium with said T-even phage comprising said foreign DNA encoding a useful polypeptide;
   (e) producing said useful polypeptide by culturing said second Gram negative bacterium;
   (f) lysing said second Gram negative bacterium; and
   (g) recovering said useful polypeptide.

12. A process, according to claim 11, wherein said DNA fragment from a T-even bacteriophage is stably propagated in a Gram negative bacterium.

13. A process, according to claim 11, wherein said Gram negative bacterium is of the genus *Shigella*.

* * * * *

UNITED STATES PATENT AND TRADEMARK OFFICE
CERTIFICATE OF CORRECTION

PATENT NO. : 4,845,031
DATED : July 4, 1989
INVENTOR(S) : David A. Shub, Nancy J. Casna It is certified that error appears in the above-identified patent and that said Letters Patent is hereby corrected as shown below:

| | |
|---|---|
| Column 2: | line 27: "T4:" should read --T4;--; line 56: "uracil," should read --uracil;--; line 58: "galactomide" should read --galactoside--. |
| Column 4: | line 3: "(gene30$^-_{am}$) p" should read --(gene30$^-_{am}$) was--; line 22: "S$_l$" should read --S1--; line 25: "ZnSO$_{40}$" should read --ZnSO$_4$--. |
| Column 5: | lines 43-44: "lysateisopyc-nic" should read --lysate-isopycnic--. |
| Column 7: | line 1: "result i" should read --result is--. |
| Column 8: | line 62: "M$_r$-value" should read --$M_r$-value--. |
| Column 9: | line 10: "M$_r$ standards" should read --$M_r$ standards--. |
| Column 10: | line 27: "mutation In addition" should read --mutation. In addition--; line 45: "487-560" should read --487-560.-- |
| Column 12: | line 25: "We" should read --A--; line 44: "ending" should read --encoding--. |

Signed and Sealed this

Thirteenth Day of November, 1990

*Attest:*

HARRY F. MANBECK, JR.

*Attesting Officer*      *Commissioner of Patents and Trademarks*